United States Patent [19]

Kato

[11] Patent Number: 5,467,781
[45] Date of Patent: Nov. 21, 1995

[54] CONDOM

[76] Inventor: Kazuyuki Kato, 5-5, Shintenchi, Naka-ku, Hiroshima-shi, Japan

[21] Appl. No.: 321,996

[22] Filed: Oct. 12, 1994

[51] Int. Cl.⁶ .................................................. A61F 6/04
[52] U.S. Cl. ........................................ 128/844; 128/918
[58] Field of Search ............................ 128/842, 844, 128/918; 604/347–353

[56] References Cited

U.S. PATENT DOCUMENTS

| | | | |
|---|---|---|---|
| 4,829,991 | 5/1989 | Boeck | 128/844 |
| 4,919,149 | 4/1990 | Stang | 128/844 |
| 4,977,903 | 12/1990 | Haines | 128/844 |
| 5,025,800 | 6/1991 | Zelson | 128/844 |
| 5,082,004 | 1/1992 | Reddy | 128/844 |
| 5,109,871 | 5/1992 | Thornton | 128/844 |
| 5,111,831 | 5/1992 | Foggia | 128/844 |
| 5,284,158 | 2/1994 | Mallette | 128/844 |
| 5,327,911 | 7/1994 | Pien | 128/918 |

FOREIGN PATENT DOCUMENTS 3-501021  3/1991  Japan.

*Primary Examiner*—Michael A. Brown
*Attorney, Agent, or Firm*—Kanesaka & Takeuchi

[57] ABSTRACT

A condom disperses local tightening force at the opening end portion and maintains wind-up property. Further, it enables the drug to be automatically applied when it is being used to effectively prevent infection of diseases. The condom has a sperm reservoir at an end portion thereof and extends in a cylindrical form, wherein an open end portion includes elastic annular trapezoidal portions in cross section with notch and an elastic annular end with a hollow end portion. The condom may have sol type active drug in the porous hollow end portion, so that said drug is applied to the outer surface of the cylindrical portion when the condom is used.

3 Claims, 1 Drawing Sheet

CONDOM

BACKGROUND OF THE INVENTION

Field of the Invention

The present invention relates to condom which is a contraceptive utensil or a sanitary utensil. More specifically, the present invention relates to condom having improved tightening function at the opening end.

Prior Art

Condoms have long been used as highly safe contraceptive utensils but the use has slightly declined due to widespread use of contraceptive pills for women and the like.

From the standpoint of protection against the spread of AIDS and prevention of infectious disease or sanitation, however, condoms are drawing attention again and their use is increasing.

A variety of contrivances have been made for the conventional condoms to enhance safety and convenience for use. For instance, Japanese Utility Model Laid-Open (Kokai) No. 33618/1991 discloses a condom in which the opening end is made thicker than the central portion thereof (FIGS. 4 and 5). According to this prior art, there is described that in using the condom, the opening end does not strongly press the root portion of penis in the radial direction and does not enter into the vulva. Strongly pressing the root portion of penis in the radial direction is not surely desirable from the standpoint of blood circulation and provides uncomfortable feeling. Therefore, the above-mentioned improvement is quite desirable. In order to maintain wind-up property, however, the annular end portion could not be omitted.

However, a study of the sectional view of the embodiment of the above prior art teaches that the inner diameter at the opening end 5A is greater by about 50% than that of the central portion and the tightening during the use is rather insufficient to possibly cause leakage of sperm or escape of condom. In regard to these points, the conventional products earlier than that of Japanese Utility Model Laid-Open (Kokai) No. 33618/1991 were rather superior.

From the standpoint of sanitation, furthermore, AIDS must be prevented, and it is necessary not only to avoid direct contact between sexual organs of both sexes (inclusive of the cases of the same sex) using latex or the like but also to positively attack malignant viruses with active drug. At the present moment, however, condoms that easily exhibit such functions have not yet been proposed.

The present inventor therefore has conducted keen study in an effort to accomplish tightening function at the opening end, pressure dispersing function and winding function, and have arrived at the present invention. Moreover, the present inventor has arrived at the present invention through efforts for obtaining a condom that makes it possible to automatically apply active drug and that is very effective from the standpoint of preventing infectious diseases and sanitation.

The object of the present invention is to provide a condom which disperses the local tightening force at the opening end portion and maintains wind-up property.

Another object of the present invention is to provide a condom which enables the active drug to be automatically applied as it is expanded and is fitted to the penis to effectively prevent infectious diseases such as AIDS and the like.

SUMMARY OF THE INVENTION

The present invention provides a condom which has a sperm reservoir at an end portion thereof and extends in a cylindrical form, wherein an opening end portion comprises an elastic annular portion of a trapezoidal shape in cross section with a notch for tightening and an elastic annular portion of a hollow tubular shape in cross section for winding. Further, in a second aspect of the invention, a solated active drug that attacks human immunodeficiency virus HIV is contained in the porous hollow tubular elastic annular portion, so that the drug is applied to the outer surface of the cylindrical portion as the condom is expanded for usage.

DESCRIPTION OF THE PREFERRED EMBODIMENT

The invention will now be described in detail by way of an embodiment.

Figure 1:
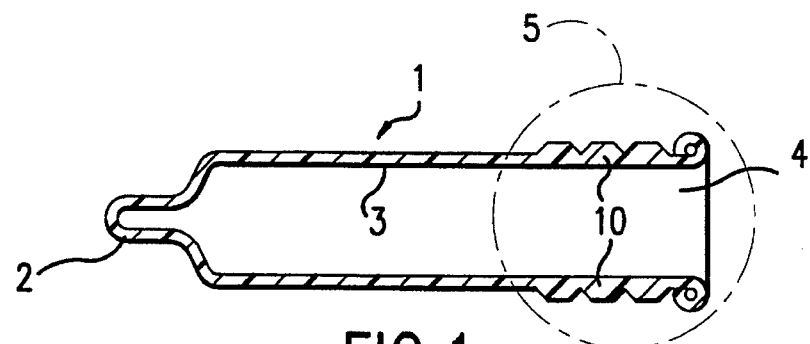
FIG. 1 is a sectional view in an expanded condition for illustrating an embodiment of the present invention.
Figure 2:
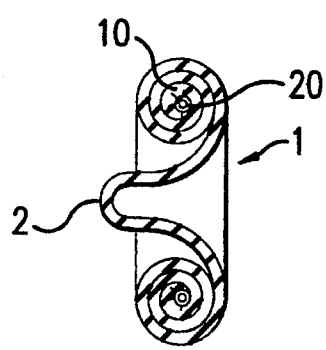
FIG. 2 is a sectional view of the embodiment of the present invention in a wound condition.
Figure 3:
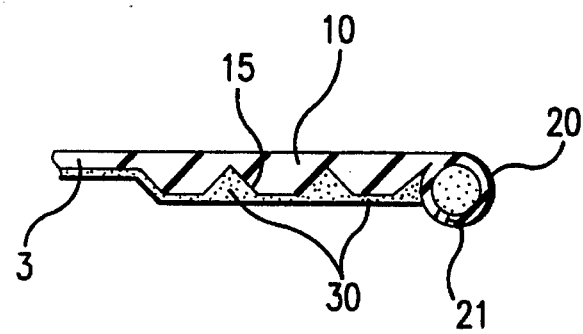
FIG. 3 is an enlarged sectional view illustrating a major portion of the embodiment of the present invention.
Figure 4:
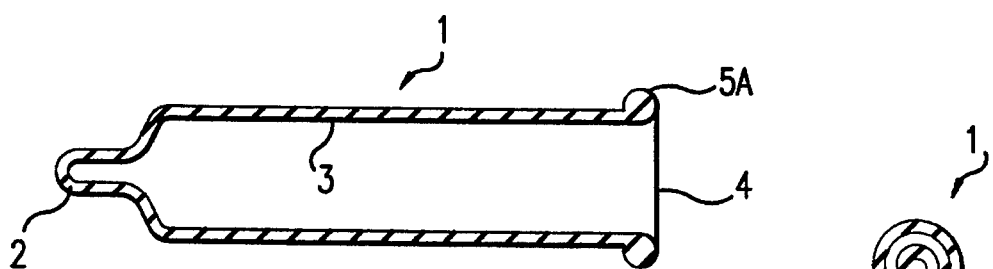
FIG. 4 is a sectional view of a prior art in an expanded condition.
Figure 5:
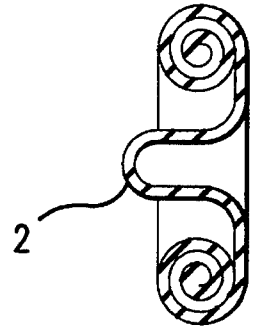
FIG. 5 is a sectional view of the prior art in a wound condition.

FIG. 1 is a sectional view of an embodiment of the present invention in an expanded state, FIG. 2 is a sectional view of the embodiment in a wound state, and FIG. 3 is a sectional view illustrating an opening end portion in an enlarged scale.

In FIGS. 1, 2, 3 and 4, reference numeral 1 denotes a condom, 2 denotes an end portion, 3 denotes a cylindrical drum portion, 4 denotes an opening portion, 5 denotes an opening end portion, 10 denotes an elastic annular portion having trapezoidal portions for fastening, 15 denotes notches, 20 denotes an elastic annular portion of a hollow tubular shape in cross section for winding, and 30 denotes a solated active drug.

In the embodiment shown in FIGS. 1, 2 and 3, an open end portion 5 includes the elastic annular portion 10 with the trapezoidal portions in cross section for tightening, and an elastic annular portion 20 of a hollow tubular shape in cross section for winding. The annular portion 10 for tightening has a plurality of notches 15 to form trapezoidal portions. Namely, as shown in FIG. 3, the annular portion 10 has a thickness greater than that of the cylindrical drum portion 3, and the notches 15 extend inwardly from the outer surface of the annular portion 10. Thus, a portion surrounded by the notches 15 forms a shape similar to trapezoid. Since the annular portion 10 is thicker than the cylindrical drum portion 3, when the condom is worn, the annular portion 10 provides wide elastic tightening pressure. Furthermore, the annular portion 20 for winding is an air-tight or a porous hollow annular portion which may remain hollow, or may be porous and contain therein a sol-type active drug. The active drug is obtained by adding, for example, an inhibitor such as suramin sodium of the like that attacks human immunodeficiency virus HIV, to vaseline (Japanese Patent Publication (KOHYO) No. 3-501021 corresponding to WO90/01935).

In a state of being wound-up, which is maintained until the product is used by a user, the active drug does not come into contact with air. When the product is expanded for usage by unwinding over a penis and is pressurized, the drug oozes out as shown in FIG. 3 through holes 21 and is applied up to the end portion of the condom. In addition to the above-mentioned active drug, the drug contained therein may be a spermicidal agent. A lubricating agent may be used instead of the drug.

The above-mentioned objects are all accomplished by the present invention.

That is, there is provided a condom which disperses the local tightening force at the opening end portion and maintains wind-up property.

There is further provided a condom which enables the active drug to be automatically applied when it is being used to make it possible to effectively prevent infection of diseases such as AIDE and the like.

What is claimed is:

1. A condom comprising:

a cylindrical main portion, a sperm reservoir formed at one end of the cylindrical main portion, and an open end portion formed at the other end of the cylindrical main portion, said open end portion including an elastic annular end and an elongated annular portion located between the annular end and the cylindrical main portion, said elongated annular portion having a thickness substantially greater than a thickness of the main portion and a plurality of annular V-shape notches arranged parallel to each other, each notch extending radially inwardly from an outer surface of the annular portion toward an inner surface thereof to have an open portion near the outer surface thereof so that when the condom is worn, the open end portion provides wide elasticity stronger than that at the cylindrical main portion without concentrating at one portion.

2. A condom according to claim 1, wherein said elastic annular end has a hollow portion to retain a material therein, and a plurality of pores so that when the condom, which is wound from the open end portion when formed, is unwound in use, the material in the hollow portion oozes through the pores and is spread at the open end portion.

3. A condom according to claim 2, wherein said material is selected from a group consisting of a lubricating agent, sol-type active drug and a spermicidal agent.

* * * * *